US012599571B2

(12) United States Patent
Hahn et al.

(10) Patent No.: US 12,599,571 B2
(45) Date of Patent: Apr. 14, 2026

(54) METHOD FOR PREPARING POLYDOPAMINE NANOMOTOR USING UREASE, AND USE OF SAME

(71) Applicant: POSTECH RESEARCH AND BUSINESS DEVELOPMENT FOUNDATION, Pohang-si (KR)

(72) Inventors: Sei Kwang Hahn, Seoul (KR); Hyun Sik Choi, Gimhae-si (KR); Sang Baie Shin, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 761 days.

(21) Appl. No.: 17/905,821

(22) PCT Filed: Mar. 10, 2020

(86) PCT No.: PCT/KR2020/003314
§ 371 (c)(1),
(2) Date: Sep. 7, 2022

(87) PCT Pub. No.: WO2021/182654
PCT Pub. Date: Sep. 16, 2021

(65) Prior Publication Data
US 2023/0122688 A1     Apr. 20, 2023

(51) Int. Cl.
| | |
|---|---|
| *A61K 9/51* | (2006.01) |
| *A61K 45/06* | (2006.01) |
| *A61K 47/18* | (2017.01) |
| *A61K 47/69* | (2017.01) |
| *A61P 13/10* | (2006.01) |
| *A61P 35/00* | (2006.01) |
| *B82Y 5/00* | (2011.01) |

(52) U.S. Cl.
CPC ............... *A61K 9/51* (2013.01); *A61K 45/06* (2013.01); *A61K 47/18* (2013.01); *A61K 47/69* (2017.08); *A61P 13/10* (2018.01); *A61P 35/00* (2018.01); *B82Y 5/00* (2013.01)

(58) Field of Classification Search
CPC .......... A61K 9/51; A61K 45/06; A61K 47/18; A61K 47/69; A61K 9/5138; A61K 31/00; A61K 47/6925; A61P 13/10; A61P 35/00; B82Y 5/00
See application file for complete search history.

(56) References Cited

FOREIGN PATENT DOCUMENTS

KR     10-2019-0047448     5/2019

OTHER PUBLICATIONS

KIPO, PCT Search Report of PCT/KR2020/003314 dated Dec. 7, 2020.

Caihong Tao et al., "Preparation and adsorption performance research of large-volume hollow mesoporous polydopamine microcapsules", MRS Communications (2019), 9, 744-749, doi: 10.1557/mrc.2019.51 (abstract only).

Ana C. Hortelão et al., "Targeting 3D Bladder Cancer Spheroids with Urease-Powered Nanomotors", ACS Nano 2019, 13, 429-439, Dec. 27, 2018, DOI: 10.1021/acsnano.8b06610.

Huy Quang Tran et al., "Synthesis of Polydopamine Hollow Capsules via a Polydopamine Mediated Silica Water Dissolution Process and Its Application for Enzyme Encapsulation", Front. Chem. 7:468., Jul. 3, 2019, doi: 10.3389/fchem.2019.00468.

Mariana Medina-Sanchez et al., "Micro- and nano-motors: the new generation of drug carriers", Ther. Deliv. (2018) 9(4), 303-316, Mar. 15, 2018.

Tom David Van Meel et al., "The effect of intravesical oxybutynin on the ice water test and on electrical perception thresholds in patients with neurogenic detrusor overactivity", Neurourol Urodyn, Mar. 2010;29(3):391-4, doi: 10.1002/nau.20785 (abstract only).

Y Sun et al., "Effects of dimethyl sulphoxide and heparin on stretch-activated ATP release by bladder urothelial cells from patients with interstitial cystitis", BJU Int. Sep. 2002;90(4):381-5, doi: 10.1046/j.1464-410x.2002.02912.x (abstract only).

Yuan Shao et al., "Intravesical Instillation of Hyaluronic Acid Prolonged the Effect of Bladder Hydrodistention in Patients With Severe Interstitial Cystitis", Urology, vol. 75, Issue 3, Mar. 2010, pp. 547-550 (abstract only).

C Lowell Parsons et al., "Successful downregulation of bladder sensory nerves with combination of heparin and alkalinized lidocaine in patients with interstitial cystitis", Urology. Jan. 2005;65(1):45-8. doi: 10.1016/j.urology.2004.08.056. (abstract only).

DY Cho et al., "The Effects of Intravesical Chemoimmunotherapy with Gemcitabine and Bacillus Calmette-Guérin in Superficial Bladder Cancer: A Preliminary Study", J Int Med Res. Nov.-Dec. 2009;37(6):1823-30. doi: 10.1177/147323000903700618. (abstract only).

Steve K Williams et al., "Intravesical therapy for bladder cancer", Expert Opin Pharmacother. Apr. 2010;11(6):947-58. doi: 10.1517/14656561003657145 (abstract only).

Shengjie Lu et al., "Mucoadhesive polyacrylamide nanogel as a potential hydrophobic drug carrier for intravesical bladder cancer therapy", Eur J Pharm Sci. May 25, 2015;72:57-68. doi: 10.1016/j.ejps.2015.03.006. Epub Mar. 13, 2015. (abstract only).

Martino Maria Zacchè et al., "Novel targeted bladder drug-delivery systems: a review", Res Rep Urol., 2015; 7: 169-178, Nov. 23, 2015. doi:10.2147/RRU.S56168.

Wei Gao et al., "Synthetic micro/nanomotors in drug delivery", Nanoscale, Issue 18, 2014 (abstract only).

Fei Peng et al., "A peptide functionalized nanomotor as an efficient cell penetrating tool", Chemical Communications, Issue 6, 2017 (abstract only).

Fei Peng et al., "Nanomotor-Based Strategy for Enhanced Penetration across Vasculature Model", Advanced Functional Materials, vol. 28, Issue 25, Jan. 15, 2018, https://doi.org/10.1002/adfm.201706117.

(Continued)

*Primary Examiner* — Jessica Worsham
(74) *Attorney, Agent, or Firm* — LEX IP MEISTER, PLLC

(57) ABSTRACT

The present invention relates to a biocompatible polydopamine nanomotor capable of infiltrating a bladder wall in a biological environment and remaining inside a bladder for a long time.

10 Claims, 9 Drawing Sheets

(56) References Cited

OTHER PUBLICATIONS

Wei Gao et al., "Artifi cial Micromotors in the Mouse's Stomach: A Step toward in Vivo Use of Synthetic Motors", ACS Nano 2015, 9, 1, 117-123, Dec. 30, 2014, https://doi.org/10.1021/nn507097k.

Berta Esteban-Fernández de Ávila et al., "Micromotor-enabled active drug delivery for in vivotreatment of stomach infection", Nat Commun. Aug. 16, 2017;8(1):272. doi: 10.1038/s41467-017-00309-w (abstract only).

Jinxing Li et al., "Micromotors Spontaneously Neutralize Gastric Acid for pH-Responsive Payload Release", Angew Chem Int Ed Engl. Feb. 13, 2017;56(8):2156-2161. doi: 10.1002/anie.201611774 (abstract only).

Xiaoli Wei et al., "Biomimetic Micromotor Enables Active Delivery of Antigens for Oral Vaccination", Nano Lett. 2019, 19, 3, 1914-1921, Feb. 6, 2019 (abstract only).

Zhiguang Wu et al., "A microrobotic system guided by photoacoustic computed tomography for targeted navigation in intestines in vivo", Sci Robot. Jul. 31, 2019;4(32):eaax0613. doi: 10.1126/scirobotics. aax0613. (abstract only).

Minfeng Zhou et al., "Self-Propelled and Targeted Drug Delivery of Poly(aspartic acid)/Iron-Zinc Microrocket in the Stomach", ACS Nano 2019, 13, 2, 1324-1332, Jan. 28, 2019 (abstract only).

Wenping He et al., "Guidable Thermophoretic Janus Micromotors Containing Gold Nanocolorifi ersfor Infrared Laser Assisted Tissue Welding", Advanced Science, vol. 3, Issue 12, Sep. 1, 2016.

Zhiguang Wu et al., "A swarm of slippery micropropellers pen-etrates the vitreous body of the eye", Science Advances, vol. 4, No. 11, Nov. 2, 2018, DOI: 10.1126/sciadv.aat4388.

[FIG. 1A]
(a)
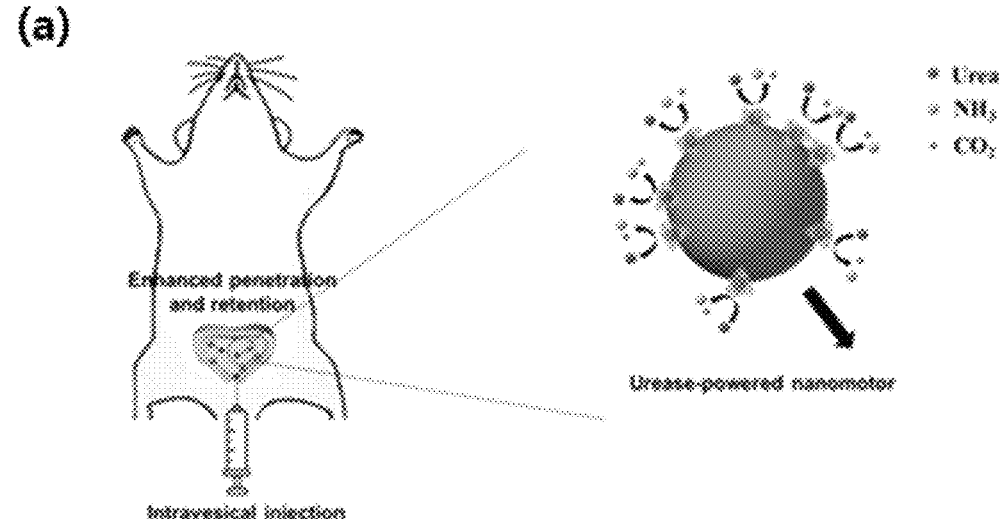
[FIG. 1B]
(b)
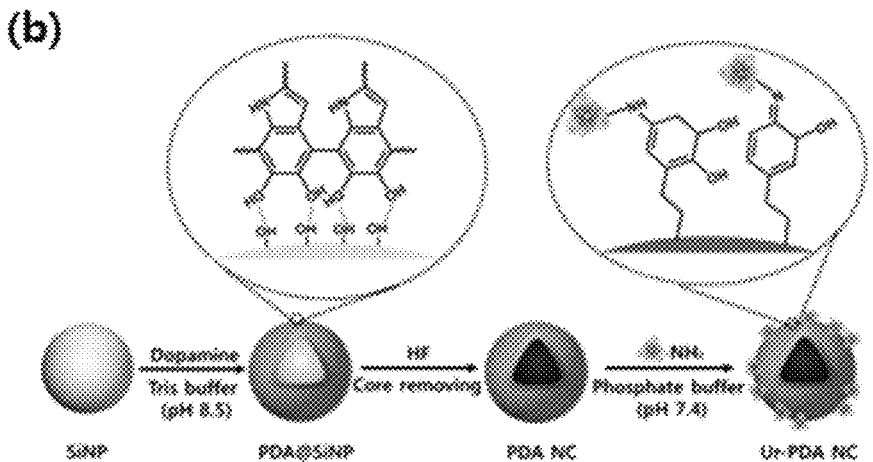

[FIG. 2]
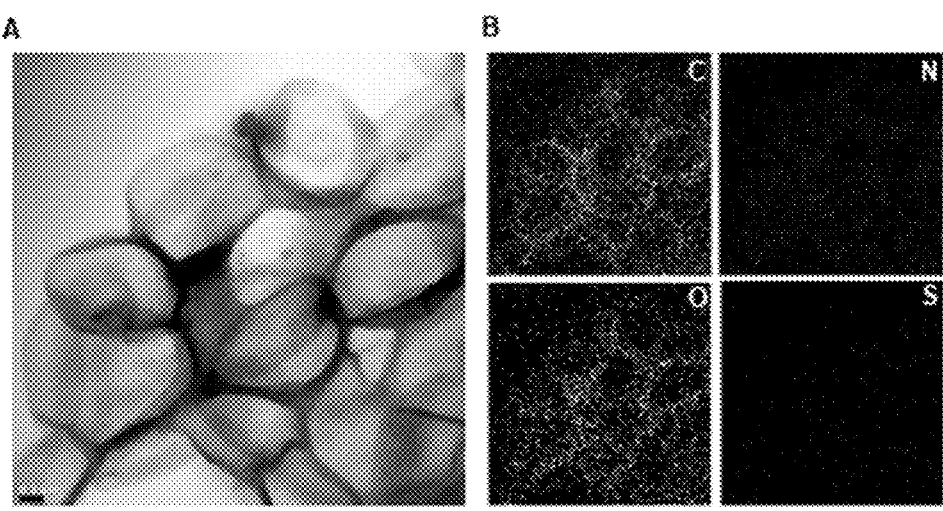

[FIG. 3A]
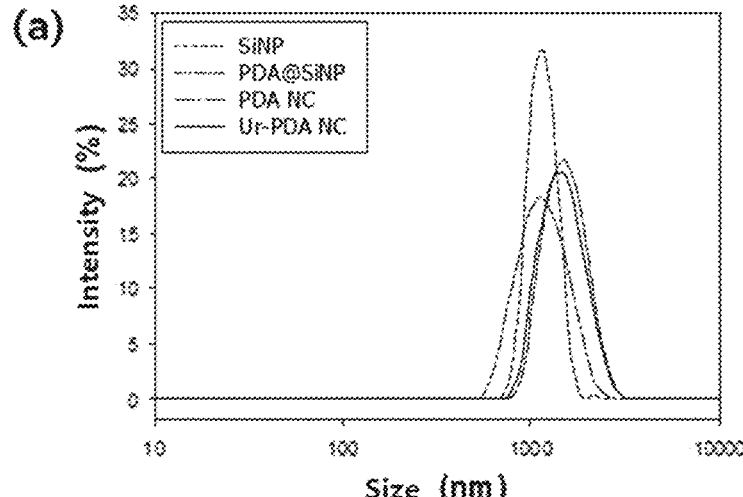
[FIG. 3B]
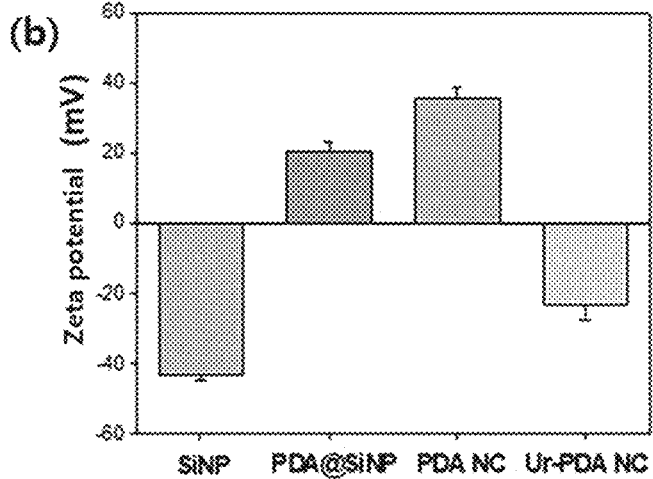

[FIG. 3C]
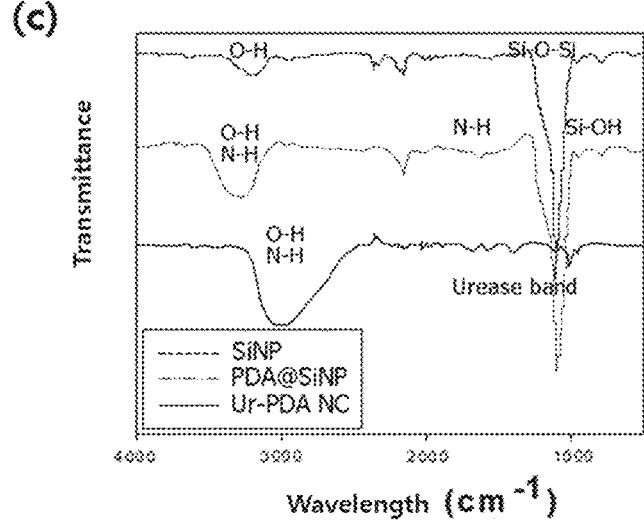
[FIG. 3D]
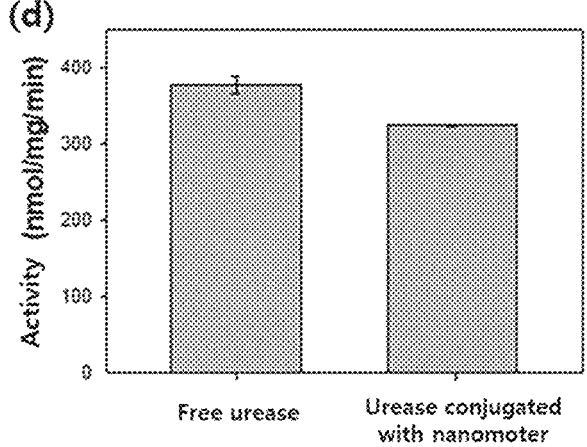

[FIG. 4A]
(a)
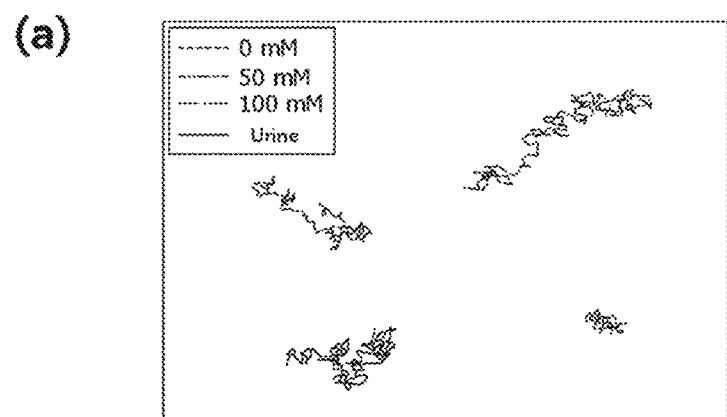
[FIG. 4B]
(b)
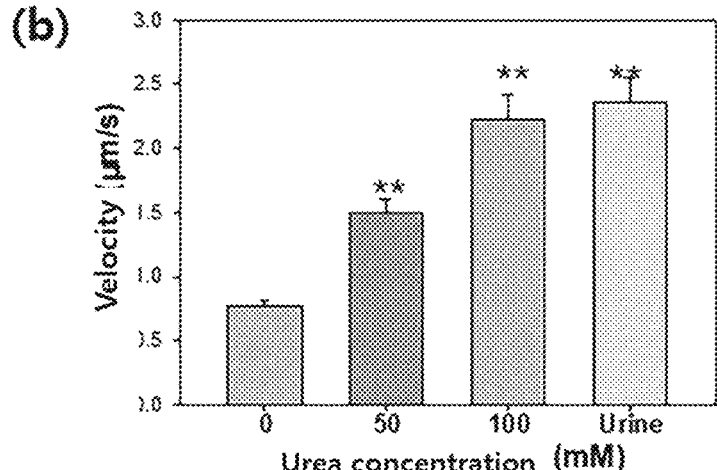

[FIG. 4C]
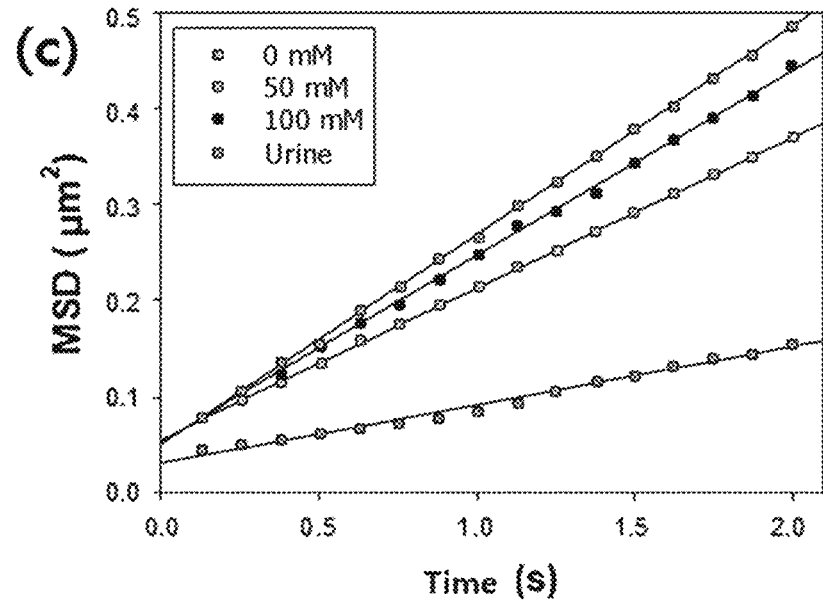
[FIG. 4D]
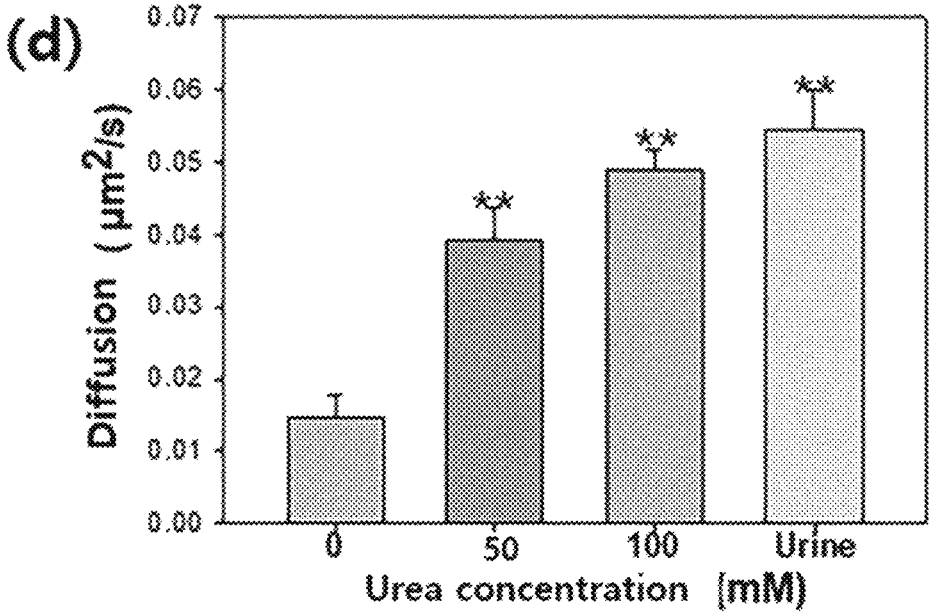

[FIG. 5]
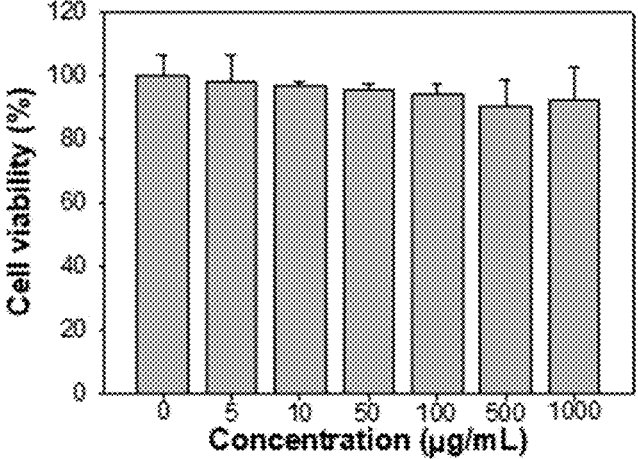
[FIG. 6]
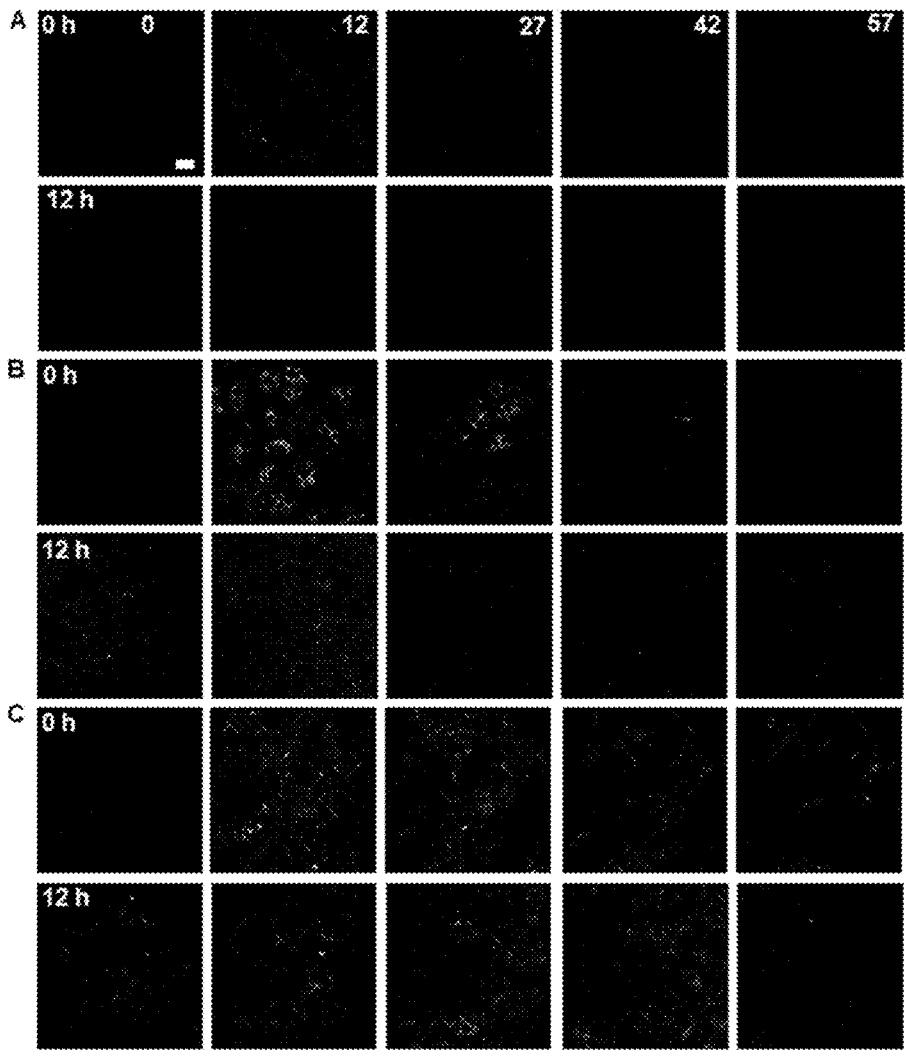

[FIG. 7]
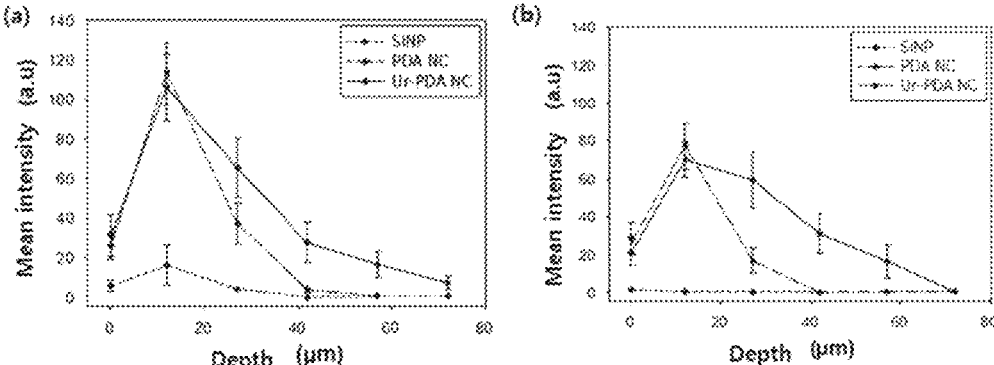
[FIG. 8]
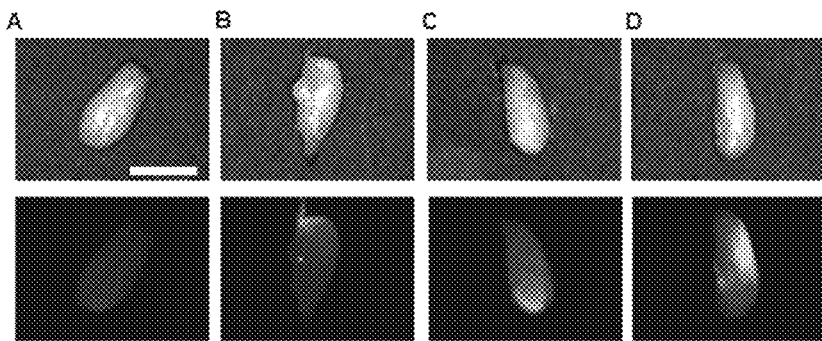
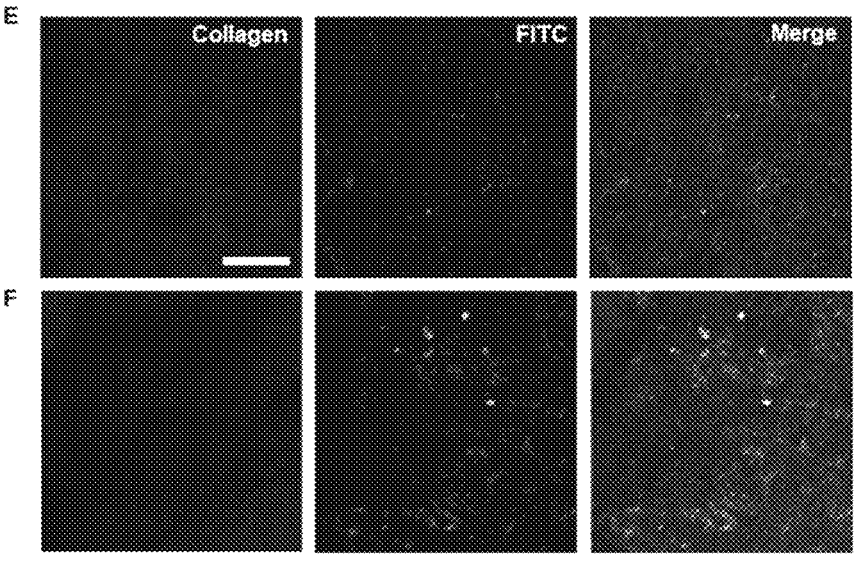

[FIG. 9]
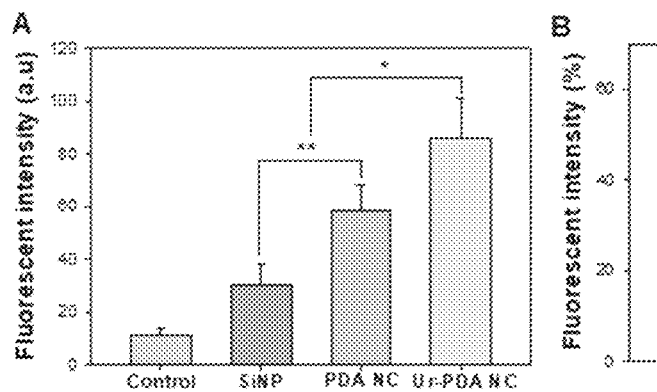
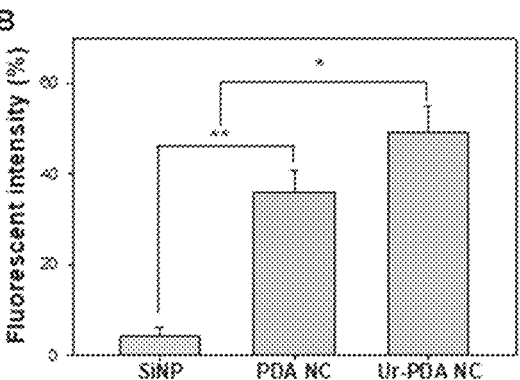
[FIG. 10]
A                                                    B
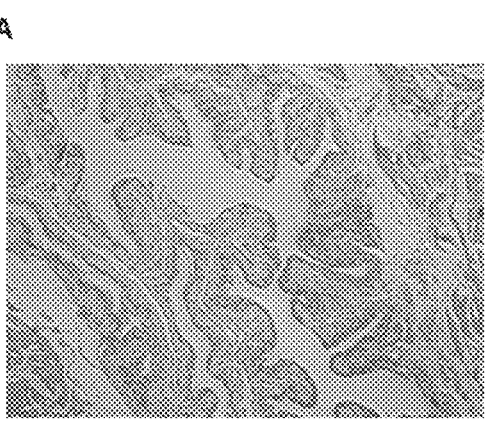
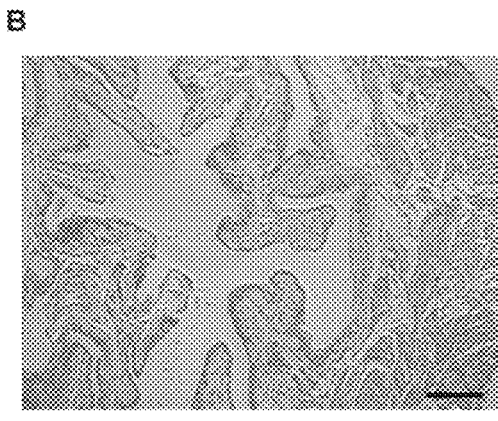

METHOD FOR PREPARING POLYDOPAMINE NANOMOTOR USING UREASE, AND USE OF SAME

BACKGROUND

1. Field of the Invention

The present invention relates to a polydopamine nano-motor using urease, a method of preparing the polydop-amine nanomotor, and a use thereof.

2. Discussion of Related Art

Intravesical therapy is a therapeutic method for directly injecting a therapeutic drug into the bladder through a catheter for the treatment of various bladder diseases, such as overactive bladder (Ref. 1), interstitial cystitis (Ref. 2-4), and bladder cancer (Ref. 5-6). Although intravesical drug delivery maximizes the therapeutic effect and minimizes systemic side effects by directly exposing bladder tissue to a therapeutic agent, it still has limitations. Due to periodic urination, such a therapeutic agent administered into the bladder can be rapidly flushed away, which necessitates frequent repeated injections for preferable therapeutic effi-cacy (Ref. 7). In addition, frequent injections of therapeutic agents can give discomfort to a patient and cause infection (Ref. 8). Therefore, the delivered drug should be able to be rapidly adhered to the bladder mucosa and retained even after urination without disrupting the function of normal cells in the bladder.

Propelled microparticles and nanoparticles, i.e., micro-motors/nanomotors, attract great attention for potential applications in nanomedicine because of advantages such as rapid drug delivery and penetration into biological barriers (Ref. 9-11). Recently, several nanomotor studies have been developed for in vivo applications. A system for delivering a drug by producing a hydrogen gas through a reaction of Zn or Mg with water and transferring it to the gastrointestinal tract was developed (Ref. 12-17). In addition, silica/$Fe_3O_4$-based micromotors whose movement is induced by a mag-netic field were also developed for in vivo applications (Ref. 18). A nanomotor system has been applied to wound closure, and an Ni-based magnetic propeller has been developed to deliver drugs to the retina through the vitreous body (Ref. 19). Although these synthetic motors showed excellent performance in an organ or tissue, compared to conventional passive targeted particles, synthetic micromotors are made of inorganic materials or metals that are not suitable for a biological system, and there is no in vivo application to other organs and tissues.

SUMMARY OF THE INVENTION

To solve the above-described problems, the present inven-tion is directed to providing a biocompatible nanomotor that can penetrate through the bladder wall and can be retained in the bladder for a long time under an in vivo condition.

The present invention provides a polydopamine nanomo-tor, which includes a hollow core; and a shell containing polydopamine, wherein the polydopamine is conjugated with urease, and the urease produces a gas in the presence of urea to induce self-propulsion of the nanomotor.

In addition, the present invention provides a method of preparing a polydopamine nanomotor, which includes:

preparing a silica-polydopamine core-shell particle by forming a polydopamine shell around a silica particle;

preparing a hollow polydopamine particle by removing the silica particle in the silica-polydopamine core-shell particle; and preparing a urease-binding hollow polydopamine particle by binding urease to the particle surface.

In addition, the present invention provides a carrier for a drug delivery system, which includes the above-described polydopamine nanomotor.

BRIEF DESCRIPTION OF THE DRAWINGS

FIG. 1 shows a schematic diagram of the penetration of polydopamine nanomotors into the bladder wall and reten-tion thereof in the bladder (FIG. 1A), and a schematic diagram of the process of preparing polydopamine nanomo-tors using a silica nanoparticle (SiNP) and polydopamine (PDA) (FIG. 1B);

FIG. 2 shows (A) an HR-TEM image of Ur-PDA NC and (B) EDS maps (scale bar=200 nm; green (C), purple (N), yellow (O), and red (S));

FIG. 3 shows a hydrodynamic size distribution for each step of polydopamine nanomotor preparation (FIG. 3A), zeta potentials of SiNP, PDA@SiNP, PDA NC and Ur-PDA NC (FIG. 3B), FT-IR spectra of SiNP, PDA@SiNP and Ur-PDA NC (FIG. 3C), and the activity of urease conjugated to a polydopamine nanomotor and free urease (FIG. 3D);

FIG. 4 shows the trajectories of polydopamine nanomo-tors for 30 seconds in the presence of urea (0, 50 and 100 mM) in simulated urine and real urine (FIG. 4A), a speed according to an increasing concentration of urea (FIG. 4B), the mean square displacement (MSD) according to an increasing time interval, analyzed by tracking the x and y coordinates of 20 particles (polydopamine nanomotor) under each condition (0, 50, 100 mM and real urine) (FIG. 4C), and diffusion coefficient values calculated from the MSD (**$P \le 0.01$, urea vs no urea) (FIG. 4D);

FIG. 5 shows an experimental result for cytotoxicity of polydopamine nanomotors;

FIG. 6 shows two-photon microscopic images of the bladder to a depth (0, 12, 27, 42 and 57 μm) after the injection of FITC-labeled (A) SiNP, (B) PDA NC and (C) Ur-PDA NC. The fluorescence images in the first and second rows detected at 0 and 12 hours after injection, respectively (scale bar=50 μm);

FIG. 7 shows the mean fluorescence intensity of the bladder at a depth (a) after intravesical injection and (b) 12 hours after injection of a FITC-labeled group (**$P \le 0.01$, Ur-PDA NC vs PDA NC);

FIG. 8 shows intact bladder images (first row) and in vitro fluorescence images (second row) 12 hours after the injec-tion of (A) PBS, FITC-labeled (B) SiNP, (C) PDA NC and (D) Ur-PDA NC (scale bar=1 cm), and the maximum projection intensity of the bladder 12 hours after the injection of FITC-labeled (E) PDA NC and (F) Ur-PDA NC (scale bar=50 μm);

FIG. 9 shows (a) the fluorescence intensity of the intact bladder 12 hours after the injection of a FITC-labeled group. (b) shows that the fluorescence intensity of the bladder is reduced by comparing the results 12 hours and 0 hour after the injection of the FITC-labeled group (**$P \le 0.01$, *$P \le 0.05$, PDA NC vs SiNP and Ur-PDA NC vs PDA NC); and FIG. 10 shows the results of H&E staining for bladder tissues 12 hours after the injection of (A) PBS and (B) polydopamine nanomotors (scale bar=100 μm).

DETAILED DESCRIPTION OF EXEMPLARY EMBODIMENTS

The present invention relates to a polydopamine nanomotor, which includes a hollow core; and a polydopamine-containing shell, wherein the polydopamine is conjugated with urease, and the urease produces a gas in the presence of urea to induce self-propulsion of nanomotors.

Hereinafter, the polydopamine nanomotor of the present invention will be described in further detail.

The term "nanomotors" are nanoparticles that can be propelled by power obtained by various external stimuli, and is defined as a microscopic device having a self-propulsion force by a chemical reaction of a catalyst in a liquid. These nanomotors can contribute to solving complicated and difficult problems in an assigned task while the self-propulsion force is maintained in a liquid.

The polydopamine nanomotor according to the present invention includes a hollow core; and a polydopamine-containing shell.

The polydopamine nanomotor of the present invention has hollow nanoparticles or nanocapsules. That is, the core of the nanomotor is hollow. By forming the core hollow, the weight of the polydopamine nanocore may be minimized, and the speed of the nanomotors may be maximized. In addition, through this, the penetration effect of the nanomotors into the mucosa may be maximized.

The shell of the present invention contains polydopamine. Dopamine, which is the monomeric form of polydopamine, is a mimetic molecule of the 3,4-dihydroxy-lphenylalanine (L-DOPA) molecule found in sea mussels. The polydopamine has catechol and imine groups forming a covalent bond, and thus can form a very strong bond not only on an organic material such as a biomaterial or a synthetic polymer, but on a solid surface such as an electrode or separator of a battery. Accordingly, it is possible to achieve surface reforming, make surface modifications, and to form a self-assembled multilayer or a nanocomposite thin film. The catechol group of the dopamine is easily oxidized in the presence of oxygen, and polydopamine shells with various thicknesses may be formed by self-polymerization.

The polydopamine of the present invention may form a covalent/non-covalent bond with target tissue, that is, mucosal tissue, thereby exhibiting high adhesive force to the tissue.

In one embodiment, the polydopamine may be a self-polymer of dopamine.

In one embodiment, the polydopamine on the shell surface may be conjugated with a bioenzyme. The polydopamine may form a bond with a bioenzyme through a covalent bond or hydrogen bond, and specifically, a catechol group of the polydopamine may form a bond with an amine group of the bioenzyme. Here, the bond may be made by the Michael addition and/or the Schiff base reaction.

The bioenzyme is a bioavailable enzyme, and a protein catalyst that mediates a chemical reaction in the body. As a bioenzyme, urease may be used.

The urease is an enzyme that hydrolyzes urea. The urease may serve as an engine to move the nanomotor while decomposing urea present at a high concentration in the bladder, and also has biocompatibility. Urea may be decomposed into ammonia and carbon dioxide by the urease.

In one embodiment, the polydopamine nanomotor may produce a gas by the action of a bioenzyme to induce self-propulsion.

When the bioenzyme is urease, the urease may generate carbon dioxide by decomposing the urea in a urea environment, and the nanomotor may be propelled and driven through the generated carbon dioxide. This allows the nanomotors to be adhered to a mucous membrane such as the bladder wall, and also penetrate into the mucous membrane. Therefore, when the urease is used, the polydopamine nanomotor may be expressed as a urease-conjugated polydopamine nanomotor or a urease-powered polydopamine nanomotor.

In one embodiment, the thickness of the shell may range from 10 to 30 nm or 15 to 25 nm. In the above thickness range, excellent biocompatibility may be imparted, and the speed of the nanomotors may be maximized by minimizing the weight of the nanomotor.

In addition, the size of the polydopamine nanomotor may range from 800 to 1,500 nm or 1,000 to 1,200 nm. In the above size range, there is an advantage of ease of bio-adhesion and bio-penetration. When the size is too small, the nanomotor cannot achieve an appropriate propulsion force, whereas when the size is too large, there is a possibility of degrading bio-penetration.

In one embodiment, the polydopamine nanomotor may further include a drug. Here, the drug may form a bond with the polydopamine of the shell. The drug may form a bond with polydopamine by x-n stacking and hydrophobic bonding The type of drug is not particularly limited, and in the present invention, may be an anticancer agent. As the anticancer agent, one or more selected from the group consisting of paclitaxel, taxotere, adriamycin, endostatin, angiostatin, mitomycin, bleomycin, cisplatin, carboplatin, doxorubicin, daunorubicin, idarubicin, 5-fluorouracil, methotrexate, and actinomycin-D may be used.

In one embodiment, the polydopamine nanomotor may be used for the treatment of a bladder disease. Here, the type of bladder disease is not particularly limited, and for example, may be selected from the group consisting of overactive bladder, interstitial cystitis and bladder cancer.

Generally, the treatment of a bladder disease uses a method of injecting a drug using a catheter into the bladder, and here, the drug does not adhere well to the bladder wall and is washed away by frequent urination, so its durability is degraded. In the present invention, using the polydopamine nanomotor, when the polydopamine nanomotor is injected into the bladder, the nanomotor is propelled by a high urea concentration in the bladder, and it may efficiently penetrate a mucosal layer of the bladder wall. In addition, it may be present in the bladder wall longer after urination. The enhanced penetration and retention of the nanomotor suggests that the nanomotor can be used as a novel method for treating various bladder diseases.

In addition, the present invention relates to a method of preparing the above-described polydopamine nanomotor.

The polydopamine nanomotor according to the present invention may be prepared by preparing a silica-polydopamine core-shell particle by forming a polydopamine shell around a silica particle;

preparing a hollow polydopamine particle by removing the silica particle from the silica-polydopamine core-shell particle; and preparing a urease-binding hollow polydopamine particle by binding urease to the surface of the hollow polydopamine particle.

In the present invention, the preparation of a silica-polydopamine core-shell particle is a step for forming a polydopamine shell around a silica particle. The silica-polydopamine core-shell particle may be expressed as PDA@SiNP.

This step may be performed by suspending the silica particle in a dopamine precursor solution, and the dopamine precursor may be self-polymerized on the silica particle, thereby preparing polydopamine.

Specifically, dopamine is self-polymerized in the presence of a buffer solution with a pH of approximately 8.5, and the polydopamine formed by the above process has very strong reactivity, and thus new bonds can be easily made on its surface.

In one embodiment, the average particle diameter of the silica particles may be 800 to 2,000 nm or 1,000 to 1,500 nm.

In one embodiment, the dopamine precursor may be dopamine hydrochloride.

In one embodiment, the content of the dopamine precursor may be 60 to 90 or 70 to 80 parts by weight with respect to 100 parts by weight of the silica particles.

In one embodiment, the reaction may be performed at 20 to 30° C. or room temperature for 8 to 15 hours or 10 to 13 hours. Since the polydopamine is self-polymerized at room temperature, it has the advantage of being able to be coated without an additional reagent or equipment, so the production process costs and process efficiency are excellent.

In one embodiment, after performing the above step, the unreacted dopamine precursor may be removed by centrifugation and/or washing.

In the present invention, the preparation of a hollow polydopamine particle is a step for removing a silica particle from the silica-polydopamine core-shell particle. The hollow polydopamine particle may be expressed as PDA NC.

This step may be performed by immersing the silica-polydopamine core-shell particle prepared in the above-described step in an acidic solution. The silica particle, which is a core, may be removed in this step.

In one embodiment, the acidic solution may include HF and $NH_4F$. In addition, the pH of the acidic solution may be 3 to 6.

In one embodiment, the step may be performed for 3 to 10 minutes or 5 to 7 minutes.

In the present invention, the step of preparing a urease-binding hollow polydopamine particle is a step for binding urease on the surface of the hollow polydopamine particle. The urease-binding hollow polydopamine particle may be a polydopamine nanomotor, and may be expressed as a urease-conjugated (or -binding) nanocapsule (or nanomotor) or Ur-PDA NC.

The step may be performed by adding a PDA NC-containing aqueous solution to a urease solution, and through the above step, a catechol group of the polydopamine of PDA NC may form a bond with an amine group of urease through the Michael addition and/or the Schiff base reaction.

In one embodiment, the reaction may be performed at 20 to 30° C. or room temperature for 8 to 15 hours or 10 to 13 hours.

In the method of preparing a polydopamine nanomotor according to the present invention, binding a drug to the surface of the hollow polydopamine particle may be further performed. Here, the binding of the drug to the polydopamine may be performed after urease binding, but it is also possible to bind the drug first before urease binding.

In one embodiment, the drug may form a bond with polydopamine by π-π stacking and hydrophobic interaction.

In one embodiment, the drug may be any of the aforementioned types.

In addition, the present invention relates to a use of the above-described polydopamine nanomotor.

The polydopamine nanomotor according to the present invention may be used as a carrier for a drug delivery system. In addition, the polydopamine nanomotor may be coated on a medical tool such as a catheter and injected into the body.

The polydopamine nanomotor may contain a drug, and the drug may be delivered into the body through the mucosa by the propulsion of the nanomotor. Here, the drug may be any of the aforementioned types.

The polydopamine nanomotor of the present invention may be used in treatment of various diseases according to the type of drug, and specifically, used in treatment of a bladder disease. The bladder disease may be selected from the group consisting of overactive bladder, interstitial cystitis and bladder cancer.

In one embodiment of the present invention, a hollow nanoparticle (nanomotor) was manufactured using polydopamine. The polydopamine may exhibit a high adhesive force to tissue by forming covalent/non-covalent bonds with the target tissue. In addition, to propel the nanomotor, urease, which is an enzyme, was conjugated on the surface of the polydopamine nanomotor. The nanomotor driven by urease was propelled while degrading urea present at a high concentration (~300 mM) in the bladder into carbon dioxide and ammonia. After injection into the bladder using a catheter, it was confirmed that nanomotors penetrate into the bladder wall by a propulsion force and a large amount of the nanomotors still remain after urination.

Hereinafter, the present invention will be described in detail with reference to the following examples. The following examples are merely provided to exemplify the present invention, and the contents of the present invention are not limited to the following examples.

EXAMPLES

<Reference> Statistical Analysis

Statistical analysis was performed through a t-test using SigmaPlot10.0 software. The value of **$P<0.01$ was considered statistically significant. Data is expressed as mean±standard deviation (SD) from several individual experiments. All experiments were performed in triplicate and 20 nanomotors were measured for each group.

Example 1. Synthesis of Polydopamine Nanomotor (1) Synthesis of Polydopamine Nanocapsule (PDA NC)

5 mg of silica particles (5 wt %) were washed with a 10 mM Tris buffer solution (pH 8.5) three times and centrifuged, thereby forming a pellet. The produced pellet was resuspended in 2 mL of a dopamine hydrochloride solution (2 mg $mL^{-1}$). The suspension became darker within 10 minutes, and this reaction was allowed to proceed for 12 hours. Afterward, the tan-colored particles were centrifuged (1000 g, 30 sec) and washed with a fresh Tris buffer solution to remove excess unreacted dopamine. PDA NC was manufactured through a centrifugation/redispersion process (4500 g for 5 min, 3 cycles) after removing the silica core with a 2M HF/8 M $NH_4F$ solution (pH 5) at 20° C. for 5 minutes.

(2) Synthesis of Urease-Conjugated Polydopamine Nanomotor (Ur-PDA NC)

An aqueous solution containing the PDA NC synthesized in (1) was suspended in a urease (3 mg $mL^{-1}$)—containing PBS solution. The reaction was performed at room temperature for 12 hours. Afterward, the urease-conjugated (-binding) polydopamine nanomotor (Ur-PDA NC) solution was washed with PBS three times and centrifuged (4500 g for 5 minutes).

In the present invention, FIG. 1A is a schematic diagram of the penetration of polydopamine nanomotors into the bladder wall and retention thereof in the bladder.

A urease-powered polydopamine nanomotor may be designed and prepared in a 3-step process as shown in FIG. 1B. In the first step, silica particles (SiNPs) were added to a dopamine solution in a Tris-HCl buffer (pH 8.5) to polymerize dopamine on the surface of the SiNP (PDA@SiNP). It can be seen that the silica nanoparticle is completely covered by a polydopamine film having a thickness of 20 nm. In the second step, to remove a silica core, an HF solution was added and a hollow nanocapsule was manufactured while maintaining a structural form. It can be seen that the particle size of the nanocapsule is approximately 1 μm. Afterward, the urease is conjugated on the surface of the nanocapsule by the reaction of an amine group of the enzyme with a catechol group of the polydopamine through the Schiff base reaction.

Experimental Example 1. Characterization of Urease-Conjugated Nanomotor (Ur-PDA NC)

(1) Method

First, the characteristic shape of a urease-conjugated nanomotor (Ur-PDA NC) was confirmed using a high-resolution transmission electron microscope (HR-TEM), and constituents were identified by the energy dispersive spectrum (EDS).

In addition, the size and zeta potential of the nanocapsule were measured for each synthesis step, and the modification of surface characteristics was measured by the FT-IR spectrum.

(2) Result

The HR-TEM image of the urease-conjugated nanomotor (Ur-PDA NC) is shown in FIG. 2A.

As shown in FIG. 2A, it can be seen that even after binding to urease, the nanomotor maintains the capsule shape with a hollow structure, and the size of the nanomotor is 1 μm.

The energy dispersive spectrum (EDS) result is shown in FIG. 2B.

As shown in FIG. 2B, it can be confirmed that the urease-conjugated nanomotor (Ur-PDA NC) includes carbon, nitrogen, oxygen and sulfur components. Particularly, sulfur is detected by a thiol group of the urease, confirming that the urease was conjugated to the nanomotor. The detected proportions of the carbon, nitrogen, oxygen and sulfur were 68.02, 13.93, 17.03 and 1.01%, respectively.

Meanwhile, the size of the nanocapsule for each synthesis step is shown in FIG. 3A.

As shown in FIG. 3A, it can be confirmed that the size of the nanocapsule gradually changes for each synthesis step. It can be confirmed that the size of PDA@SiNP was larger than SiNP due to polydopamine coating, and the size of the PDA NC became slightly smaller after the silica core was removed. In addition, in the final step, the size of the Ur-PDA NC became slightly larger again, which can indirectly confirm the successful conjugation of the urease.

In addition, the zeta potential analysis result of the nanocapsule for each synthesis step is shown in FIG. 3B. The zeta potential shows the charge characteristic of the nanocapsule produced in each preparation step, and the silica core shows a negative zeta potential (−43±0.87 mV), whereas it can be confirmed that PDA@SiNP shows a positive value of 20.6±0.89 mV due to the amine group on the polydopamine surface. However, after conjugation of the urease, due to the introduction of the urease molecule, the zeta potential of the nanocapsule showed a negative value (−23.5±0.70 mV).

In addition, the FT-IR spectrum measurement result is shown in FIG. 3C. The FT-IR spectrum can show the evidence of the modification of surface characteristics and successful conjugation. The strong absorption peak at 1020-1110 cm$^{-1}$ corresponds to Si—O—Si asymmetric stretching vibrations, and the peak at 960 cm$^{-1}$ is due to asymmetric bending and stretching vibrations of Si—OH. After coating with the polydopamine, new absorption peaks were observed at 1520 and 1615 cm$^{-1}$ corresponding to shear vibrations of N—H in the amide group and an aromatic ring of the dopamine. After removing the silica core and conjugating the urease, the peaks of Si—O—Si and Si—OH disappeared, and some characteristic absorption peaks of the urease having low intensity were observed in the range of 1000-1800 cm$^{-1}$.

Experimental Example 2. Urease Quantification and Analysis of Urease Activity (1) Method The concentration of the urease present on the surface of the polydopamine nanomotor was measured using a BCA protein analysis kit. The BCA protein analysis kit is used to quantify a protein amount by correlating a protein amount with a decrease in copper by a peptide bond.

In addition, the enzyme activity of the urease bound to the PDA NC was evaluated using a commercial kit for determining the concentration of ammonia produced by Berthelot's method.

Here, the concentration of the nanomotor was 0.5 mg mL$^{-1}$, and the experiment was performed according to the manufacturer's instructions.

(2) Result

The amount of the urease on the surface of the polydopamine nanomotor was quantified using a BCA protein analysis kit, and the results of comparing the activities of the urease conjugated to the nanomotor and free urease are shown in FIG. 3D.

As shown in FIG. 3D, it can be confirmed that the activity of the conjugated urease is similar (86%) to the activity of the free urease without a significant decrease. According to this, it can be confirmed that the urease can be used in the propulsion of nanomotors.

Experimental Example 3. Video Recording and Analysis of Nanomotor Motility (1) Method To observe and record a video of the movement of the polydopamine nanomotor, an optical microscope was used. Aqueous samples of the nanomotors were placed on glass slides and well mixed with various urea concentrations (0, 50 and 100 mM) and real urine. For a real urine experiment, urine was extracted from a mouse and collected in a 1.5 mL e-tube. The urine was centrifuged (8000 rpm for 5 minutes) and syringe-filtered using a 0.22-μm filter. The movement of the nanomotors including urine was recorded for 30 seconds at a frame rate of 8 fps. 20 or more nanomotors per condition were analyzed, and the tracking path, mean square displacement (MSD) and speed were analyzed using ImageJ. Afterward, the diffusion coefficient was obtained by putting MSD data to the following equation.

$$MSD(\Delta t)=4De\ \Delta t$$

Here, De indicates the effective diffusion coefficient, and Δt indicates a time interval.

(2) Result

The urease-powered nanomotor converts urea into ammonia and carbon dioxide as shown in Equation 1 below.

$$(NH_2)_2CO + H_2O \rightarrow CO_2 + 2NH_3$$

Although the geometric asymmetry of synthetic motors has been regarded as an important requirement for generating propulsion, recent studies have shown that the disproportionate distribution of molecules conjugated to a nanomotor surface is sufficient for synthetic motors propelled by the biocatalytic transformation of an enzyme. The movement profile of the urease-powered nanomotors was evaluated with urea concentrations of 0, 50 and 100 mM and real urine.

The tracking trajectories of the nanomotors are shown in FIG. 4A. The tracking trajectories were recorded for 30 seconds at 8 frames per second. In addition, a speed and a mean square displacement (MSD) were calculated from the tracked trajectories, and the results are shown in FIGS. 4B and 4C.

When there was no urea, the nanomotors randomly moved at a speed of 0.77 μm $s^{-1}$ by Brownian motion and did not showed directionality. However, after urea was added (50 and 100 mM), the nanomotors showed enhanced diffusion and directionality at speeds of 1.49 and 2.23 μm $s^{-1}$, respectively. The MSD, as the typical form of diffusion motion, increased linearly over time, and further increased with an increase in urea concentration.

Particularly, the MSD and speed of the nanomotors in real urine were higher than those of other groups, confirming that the nanomotors using urease may be effectively propelled to be applied in treatment of a bladder disease.

In addition, the effective diffusion coefficient was obtained using the MSD, which is shown in FIG. 4D. The effective diffusion coefficient was obtained by putting it to the following equation.

As shown in FIG. 4D, it can be seen that, as the urea concentration increases, diffusion increases, and diffusion rate saturation is shown at a high urea concentration. It can be seen that this is a similar behavior to that assumed by Michaelis-Menten kinetics.

Experimental Example 4. Cytotoxicity Experiment (1) Method

Before in vivo testing, after incubating human bladder cells (RT4) and nanomotors for 24 hours, the cell compatibility of the nanomotors was analyzed.

Human bladder cancer cells (RT4) were incubated at 37° C. in a humidified incubator containing 5% carbon dioxide. The bladder cancer cells were incubated in a medium containing 10% fetal bovine serum, 100 IU $mL^{-1}$ of penicillin and 100 mg $mL^{-1}$ of streptomycin. The RT4 cells were incubated for 24 hours with the nanomotors (5, 10, 50, 100, 500 and 1000 μg $mL^{-1}$), and then washed with a serum-free medium.

Cell viability was evaluated by an MTT assay. The MTT solution was prepared at a concentration of 0.5 mg $mL^{-1}$, and then sterilized using a 0.2-μm filter. Subsequently, 0.5 mL of the solution as added to each well. The wells were incubated for 30 minutes at 37° C., and 200 μL of DMSO was added. After incubation for 2 hours, absorbance was measured at a wavelength of 595 nm.

(2) Result

The cytotoxicity test result is shown in FIG. 5.

As shown in FIG. 5, it can be confirmed that the nanomotors have almost no cytotoxicity until 1,000 μg $mL^{-1}$.

Example 2. Labeling with FITC

To label PDA NC and Ur-PDA NC with an FITC fluorescence dye, 100 μL of FITC solution (1 mM) was added to 2 mL each of PDA NC and Ur-PDA NC aqueous solutions. The mixture was incubated at room temperature for 12 hours to perform a reaction. Subsequently, the labeled PDA NC and Ur-PDA NC solutions were dialyzed (3.5 kDa) for 24 hours to remove an excess of unreacted FITC molecules.

As a control, $SiO_2$ was labeled with FITC as previously reported elsewhere. 50 μL of APTES was added to 2 mL of a $SiO_2$ nanoparticle solution (5 mg $mL^{-1}$ of ethanol). After stirring for 12 hours at room temperature, modified silica nanoparticles were separated and excess APTES was removed through a centrifugation/redispersion process (1000 g, 30 sec, 3 cycles). Afterward, 1 mL of the resulting solution was mixed with 0.5 mL of an FITC ethanol solution (1 mM). After stirring for 4 hours, particles were collected by a centrifugation/redispersion process (1000 g, 30 sec, 3 cycles).

Experimental Example 5. Two-Photon Fluorescence Imaging of Nanomotors in Bladder (1) Method To investigate the ability of nanomotors to penetrate the bladder wall and remain in the bladder, an FITC fluorescent material was labeled on a motor surface. In addition, as controls, SiNP and PDA NC groups were also labeled with FITC on their surfaces.

SD female mice were randomly divided into three groups (SiNP, PDA NC, and Ur-PDA NC; n=3), and the mice were anesthetized by inhalation anesthesia. 50 μL each of FITC-labeled SiNP, PDA NC and Ur-PDA NC suspensions was administered into the bladder using a catheter. 0 hour and 12 hours after administration, the mice were sacrificed, and to observe the bladder wall, the bladder was excised and dissected. Subsequently, the resulting tissue was rinsed with PBS and flattened, and visualized using a two-photon fluorescence microscope.

The two-photon fluorescence signal of FITC and the secondary harmonic generation (SHG) of the collagen structure were observed at a wavelength of 950 nm. Images were collected as a Z-stack (xyz, 400 Hz) at 512×512 pixels and analyzed with Leica's LAS AF Lite 2.6.1.

(2) Result

FIGS. 6 and 7 show the results of visualizing and quantifying the fluorescence intensity of the bladder 0 and 12 hours after injection of the FITC-labeled groups. All mice urinated several times during the 12 hours, and all urine samples were stored and used for analysis.

It was confirmed that the SiNP group showed very low green fluorescence intensity in the bladder wall (FIG. 5A), whereas the PDA NC and Ur-PDA NC groups showed strong green fluorescence in the bladder wall (B and C in FIG. 6). Therefore, it can be demonstrated that polydopamine improves adhesion to bladder tissue.

Particularly, Ur-PDA NC was observed up to a depth of 60 μm in the bladder wall ((a) in FIG. 7). Propulsion of nanomotors may enable penetration through a mucosal layer in the bladder. Despite the decrease in fluorescence intensity, the fluorescence trend was similar even after 12 hours after injection. While the fluorescence intensity was decreased to 27 μm in the bladder wall in all groups due to urination, it can be confirmed that fluorescence deeper than 27 μm was retained even 12 hours later ((b) in FIG. 7). Accordingly, it can be confirmed that the bladder wall penetration of nanomotors is an essential requirement for longer retention in the bladder.

Experimental Example 6. In Vivo Fluorescence Imaging (1) Method

To further investigate sample retention in an intact bladder after urination, the fluorescence intensity of the whole bladder was visualized and quantified 12 hours after intrabladder injection.

SD female mice were randomly divided into four groups (control, SiNP, PDA NC, and Ur-PDA NC; n=3), the mice were anesthetized by inhalation and then FITC-labeled samples were injected into the bladder (50 μL) using a catheter. 12 hours after injection, fluorescence images were obtained in the wavelength range of 500 to 550 nm using an in vivo fluorescence imaging system. The bladder was extracted from a sacrificed mouse, dissected and then observed using an in vivo fluorescence imaging system.

(2) Result

The results are shown in FIGS. 8 and 9.

As shown in A to E in FIG. 8 and (a) in FIG. 9, it can be confirmed that the fluorescence intensity of FITC-labeled PDA NC or Ur-PDA NC is stronger than those of other groups (control and SiNP). Particularly, Ur-PDA NC showed the strongest fluorescence intensity.

In addition, as a result of comparing the fluorescence intensity of each group before and after urination, as shown in (b) in FIG. 9, it can be confirmed that the bladder fluorescence intensity of the SiNP, PDA NC and Ur-PDA NC groups after 12 hours was decreased 4.5%, 35.8% and 49.2%, respectively, and compared to other groups, a considerable amount of Ur-PDA NC remains after urination. This suggests that the urease-powered polydopamine nanomotor system may be an effective drug delivery system for a bladder disease.

Experimental Example 7. Histological Analysis (1) Method

After confirming the nanomotor retention in the bladder, histological analysis of bladder tissue was performed through H&E staining.

After injection of PBS and urease-powered nanomotors into the bladder for 24 hours, 12 hours later, the bladder was extracted from a sacrificed mouse and dissected, and then fixed in 4% paraformaldehyde. The fixed bladder was embedded in a paraffin block, and then a 4-μm section was made for H&E staining. The stained part was observed with an optical microscope.

(2) Result

The staining results are shown in FIG. 10.

As shown in FIG. 10, it can be confirmed that there is no significant difference in bladder tissue between the case of PBS injection and the case of nanomotor injection. This shows that the nanomotors have no tissue toxicity.

A polydopamine nanomotor according to the present invention may penetrate through a mucosal layer and remain in the body for a long time.

Particularly, a urease-powered polydopamine nanomotor moves autonomously in the presence of urea, and after reaching the bladder wall, is attached to bladder cells due to polydopamine on the nanomotor surface. After injection into the bladder, the nanomotor may penetrate deep into the bladder tissue by self-propulsion, so many nanomotors can be retained in the bladder after urination. Through this, the efficiency of drug delivery into the bladder is excellent, and the therapeutic effect can be maximized.

REFERENCES

1. Van Meel, T. D.; De Wachter, S.; Wyndaele, J. J. The Effect of Intravesical Oxybutynin on the Ice Water Test and on Electrical Perception Thresholds in Patients with Neurogenic Detrusor Overactivity. Neurourol. Urodyn. 2010, 29, 391-394.
2. Sun, Y.; Chai, T. C. Effects of Dimethyl Sulphoxide and Heparin on Stretch-activated ATP Release by Bladder Urothelial Cells from Patients with Interstitial Cystitis. BJU. Int. 2002, 90, 381-385.
3. Shao, Y.; Shen, Z. J.; Rui, W. B.; Zhou, W. L. Intravesical Instillation of Hyaluronic Acid Prolonged the Effect of Bladder Hydrodistention in Patients with Severe Interstitial Cystitis. Urology 2010, 75, 547-550.
4. Parsons, C. L. Successful Downregulation of Bladder Sensory Nerves with Combination of Heparin and Alkalinized Lidocaine in Patients with Interstitial Cystitis. Urology 2005, 65, 45-48.
5. Cho, D. Y.; Bae, J. H.; Moon, D. G. The Effects of Intravesical Chemoimmunotherapy with Gemcitabine and *Bacillus* Calmette-Gurin in Superficial Bladder Cancer: a Preliminary Study. J. Int. Med. Res. 2009, 37, 1823-1830.
6. Williams, S. K.; Hoenig, D. M.; Ghavamian, R.; Soloway, M. Intravesical Therapy for Bladder Cancer. Expert Opin. Pharmacother. 2010, 11, 947-958.
7. Lu, S.; Neoh, K. G.; Kang, E. T.; Mahendran, R.; Chiong, E. Mucoadhesive Polyacrylamide Nanogel as a Potential Hydrophobic Drug Carrier for Intravesical Bladder Cancer Therapy. Eur. J. Pharm. Sci. 2015, 72, 57-68.
8. Zacche, M. M.; Srikrishna, S.; Cardozo, L. Novel Targeted Bladder Drug-delivery Systems: a Review. Res. Rep. Urol. 2015, 7, 169-178.
9. Gao, W.; Wang, J. Synthetic Micro/nanomotors in Drug Delivery. Nanoscale 2014, 6, 10486-10494.
10. Peng, F.; Tu, Y.; Adhikari, A.; Hintzen, J. C. J.; Lowik, D. W. P. M.; Wilson, D. A. A Peptide Functionalized Nanomotor as an Efficient Cell Penetrating Tool. Chem. Commun. 2017, 53, 1088-1091.
11. Peng, F.; Men, Y.; Tu, Y.; Chen, Y.; Wilson, D. A. Nanomotor-based Strategy for Enhanced Penetration Across Vasculature Model. Adv. Funct. Mater. 2018, 28, 1706117.
12. Gao, W.; Dong, R.; Thamphiwatana, S.; Li, J.; Gao, W.; Zhang, L.; Wang, J. Artificial Micromotors in the Mouse's Stomach: A Step Toward In Vivo Use of Synthetic Motors. ACS Nano 2015, 9, 117-123.
13. de Avila, B. E.-F.; Angsantikul, P.; Li, J.; Lopez-Ramirez, M. A.; Ramirez-Herrera, D. E.; Thamphiwatana, S.; Chen, C.; Delezuk, J.; Samakapiruk, R.; Ramez, V.; Obonyo, M.; Zhang, L.; Wang, J. Micromotor-enabled Active Drug Delivery for In Vivo Treatment of Stomach Infection. Nat. Commun. 2017, 8, 272.
14. Li, J.; Angsantikul, P.; Liu, W.; Avila, B. E. F.; Thamphiwatana, S.; Xu, M.; Sandraz, E.; Wang, X.; Delezuk, J.; Gao, W.; Zhang, L.; Wang, J. Micromotors Spontaneously Neutralize Gastric Acid for pH-Responsive Payload Release. Angew. Chem. Int. Ed. 2017, 56, 2156-2161.

15. Wei, X.; lum, M. B. G.; Karshalev, E.; A 'vila, B. E. F.; Zhou, J.; Ran, D.; Angsantikul, P.; Fang, R. H.; Wang, J.; Zhang, L. Biomimetic Micromotor Enables Active Delivery of Antigens for Oral Vaccination. Nano Lett. 2019, 19, 1914-1921.

16. Wul, Z.; Li, L.; Yang, Y.; Hu, P.; Li, Y.; Yang, S. Y.; Wang, L. V.; Gao, W. A Microrobotic System Guided by Photoacoustic Computed Tomography for Targeted Navigation in Intestines In Vivo. Sci. Robot. 2019, 4, 24.

17. Zhou, M.; Hou, T.; Li, J.; Yu, S.; Xu, Z.; Yin, M.; Wang, J.; Wang, X. Self-Propelled and Targeted Drug Delivery of Poly(aspartic acid)/Iron-Zinc Microrocket in the Stomach. ACS Nano 2019, 13, 1324-1332.

18. He, W.; Frueh, J.; Hu, N.; Liu, L.; Gai, M.; He, Q. Guidable Thermophoretic Janus Micromotors Containing Gold Nanocolorifiers for Infrared Laser Assisted Tissue Welding. Adv. Sci. 2016, 3, 1600206.

19. Wu, Z.; Troll, J.; Jeong, H.; Wei, Q.; Stang, M.; Ziemssen, F.; Wang, Z.; Dong, M.; Schnichels, S.; Qiu, T.; Fischer, P. A Swarm of Slippery Micropropellers Penetrates the Vitreous Body of the Eye. Sci. Adv. 2018, 4, eaat4388.

What is claimed is:

1. A polydopamine nanomotor, comprising:

a hollow core; and a shell containing polydopamine, wherein the polydopamine is bound to urease, and the urease generates a gas in the presence of urea to induce self-propulsion of the nanomotor, wherein the polydopamine nanomotor has a size of 800 to 1,500 nm, and wherein the shell has a thickness of 10 to 30 nm.

2. The nanomotor of claim 1, wherein a catechol group of the polydopamine forms a bond with an amine group of the urease.

3. The nanomotor of claim 1, wherein a drug is bound to the polydopamine shell.

4. The nanomotor of claim 3, wherein the drug is an anticancer agent, which is one or more selected from the group consisting of paclitaxel, taxotere, adriamycin, endostatin, angiostatin, mitomycin, bleomycin, cisplatin, carboplatin, doxorubicin, daunorubicin, idarubicin, 5-fluorouracil, methotrexate, and actinomycin-D.

5. The nanomotor of claim 1, which is used for treating one or more bladder diseases selected from overactive bladder, interstitial cystitis and bladder cancer.

6. A method of preparing the polydopamine nanomotor of claim 1, comprising:

preparing a silica-polydopamine core-shell particle by forming a polydopamine shell around a silica particle;

preparing a hollow polydopamine particle by removing the silica particle from the silica-polydopamine core-shell particle; and preparing a urease-binding hollow polydopamine particle by binding urease to the surface of the hollow polydopamine particle.

7. The method of claim 6, wherein, in the preparing of a hollow polydopamine, the removal of silica particles is performed under an acidic condition.

8. The method of claim 6, wherein, in the preparing of a urease-binding hollow polydopamine particle, the binding of urease is formed by a Michael addition and/or a Schiff base reaction.

9. The method of claim 6, further comprising binding a drug to the surface of the hollow polydopamine particle.

10. A carrier for a drug delivery system, comprising the polydopamine nanomotor of claim 1.

\* \* \* \* \*